United States Patent [19]

Pace et al.

[11] 4,233,144
[45] Nov. 11, 1980

[54] ELECTRODE FOR VOLTAMMETRIC IMMUNOASSAY

[75] Inventors: Salvatore J. Pace, Yorktown Heights; Anand Kumar, Monroe, both of N.Y.

[73] Assignee: Technicon Instruments Corporation, Tarrytown, N.Y.

[21] Appl. No.: 30,206

[22] Filed: Apr. 16, 1979

[51] Int. Cl.² .................. G01N 27/30; G01N 33/16
[52] U.S. Cl. ........................ 204/195 B; 23/230 B; 23/915; 204/1 T; 204/195 M; 204/195 L; 424/12
[58] Field of Search ............... 23/230 B; 424/12; 204/195 B, 1 E, 195 M, 195 L

[56] References Cited

U.S. PATENT DOCUMENTS

| | | | |
|---|---|---|---|
| 3,966,580 | 6/1976 | Janata | 204/195 B |
| 3,975,238 | 8/1976 | Bean | 195/103.5 R |
| 4,081,334 | 3/1978 | Suzuki | 204/195 B X |
| 4,139,348 | 2/1979 | Swartz | 422/119 |
| 4,151,049 | 4/1979 | Janata | 204/195 B |

OTHER PUBLICATIONS

M. Cais et al., Nature, 270, 534–535, Dec. 1977.
William R. Heineman et al., Science, 204, 865–866, (May 25, 1979).

Primary Examiner—Sidney Marantz
Attorney, Agent, or Firm—S. P. Tedesco

[57] ABSTRACT

Immunoassays featuring voltammetric measurements wherein at least one of the immunoreactants is labelled with an electroactive substance. Measurement is effected on a pulsed-basis to maximize the signal change due to the electron transfer capabilities of the labelled immunoreactants.

8 Claims, No Drawings

ELECTRODE FOR VOLTAMMETRIC IMMUNOASSAY

FIELD OF THE INVENTION

This invention relates to immunoassay techniques and, more particularly, to performing a more sensitive voltammetric immunoassay.

BACKGROUND OF THE INVENTION

In the past several years, many new techniques have been developed to perform assays for biological substances. Most of the conventional procedures for performing immunoassays require the separation of unreacted constituents from the mixture after an immunoreaction has occurred. This separation step is usually cumbersome, inconvenient, and time consuming. In addition, procedures including a separation step are not well adapted for continuous flow or automated apparatuses. Therefore, it is desirable to accomplish an assay which does not require separation of bound and unbound reactants. Voltammetric analysis of immunoreactions is such an assay method.

One of the drawbacks of using voltammetric techniques for immunoassays, however, has been low sensitivity. In a recent publication from W. R. Heineman, H. B. Halsall, and C. W. Anderson, *Immunoassay by Differential Pulse Polarography*, Science, Vol. 204, Pgs. 865–866; 25 May, 1979, a voltammetric technique for performing immunoassays is described. Also, see Science, vol. 204 No. 865 (1979); and Analytical Chemistry, Vol. 51, No. 12, October, 1979. The described technique appears to be too insensitive for measuring biological samples, wherein many analytes of interest are found in very low concentrations.

Therefore, in order to provide a viable voltammetric immunoassay technique, a marked improvement in the sensitivity of the voltammetric techniques is needed. The present invention is addressed to enhancing such sensitivity.

SUMMARY OF THE INVENTION

Generally speaking, the voltammetric immunoassaying method of this invention features attaching an electrically reversible electroactive-label to one of the complementary immunoreactants of an immunoreaction (e.g., the antigen). A mixture is formed comprising at least two complementary immunoreactants, one of which is electroactively labelled, and a biological sample containing an unknown constituent, to accomplish a competitive binding-type of reaction.

The mixture is incubated to support a competitive reaction and subsequently analyzed voltammetrically. The apparatus necessary to perform such voltammetric analysis is well known in the art. For example, a typical apparatus for practicing the invention is shown in the reference to: A. J. Bard, Editor; Marcel Dekker, *Electroanalytical Chemistry*, Vol. 1 (Chapter I by D. E. Smith, Pages 1–155).

The sensitivity of the voltammetric assay is enhanced according to the invention in one of the three ways: (a) the labelled-immunoreactant comprises a plurality of electro-active groups to increase the ability of the immunoreactant molecule to transfer electrons at the electrode surface, (b) the electrode reaction of the labelled-immunoreactant is inherently more facile when immobilized directly on the electrode surface, and its immunoreaction with its complementary immunoreactant will inhibit the transfer of electrons at the electrode surface, and (c) a catalytic reaction is induced in the reactive mixture in view of the redox capability of the labelled immunoreactant to accept or donate electrons. The rapid regeneration (oxidation) of the reduced labelled immunoreactant increases its effective concentration at the monitoring electrode surface, whereby the signal output is enhanced. Accordingly, the ability of the labelled-immunoreactant molecule to effect electron transfer is increased, thus amplifying the signal change due to the reaction, and, hence, increasing the sensitivity of the electrochemical measurement.

DETAILED DESCRIPTION OF THE INVENTION

Several different reactions may be used to perform an immunoassay, but most of them are modifications of the basic "competitive binding" technique given by the following equations:

(1a) $Ab + Ag^* + Ag \rightleftharpoons Ab:Ag^* + Ab:Ag$ (1b) $Ab + Ab^* + Ag \rightleftharpoons Ab:Ag + Ab^*:Ag$ For purposes of brevity, reactions involving only the labelled antigen ($Ag^*$) will be discussed hereinafter. However, it should be apparent under certain circumstances that the same discussion could also apply to a labelled antibody $Ab^*$.

Generally speaking, there are several ways to measure immuno-reactions:

(a) $Ag^*$ can be the only measurable species by virtue of the fact that the electroactive label of the complex $Ab:Ag^*$ can, in some cases, be arranged to be inaccessible to the measuring electrode. This inaccessibility can be achieved by placement of the electroactive label upon the antigen such that, upon combining with the antibody, the label becomes inaccessible to, or blocked from, the electrode;

(b) where the labelled antigen $Ag^*$ has a lower molecular weight than its complex $Ab:Ag^*$, the diffusion rate of $Ag^*$ through the solution is higher than that of the $Ab:Ag^*$. Therefore, the magnitude of the diffusion dependent signal of the $Ag^*$ at the monitoring electrode will be greater than the magnitude of the signal of the complex. Consequently, the labelled antigen $Ag^*$ can be electrochemically distinguished from the labelled complex $Ab:Ag^*$;

(c) where the labelled antigen $Ag^*$ is linked or bound to the monitoring electrode surface, a change in signal can be detected when the $Ag^*$ binds with the antibody $Ab$ to form the complex $Ab:Ag^*$; and (d) the complex $Ab:Ag^*$ could be electroactive at a potential different from $Ag^*$ and, hence, both species are electrochemically distinguishable and independently monitored.

As aforementioned, one disadvantage of voltammetric techniques for performing immunoassays has been lack of sensitivity. In order to increase sensitivity, several enhancement techniques can be used. The sensitivity or measurement capability of the monitoring electrode may be substantially enhanced by using electrochemical relaxation techniques coupled with enhancing the electron transfer capabilities of the labelled-immunoreactant at the electrode surface. Typically, an alternating current or perturbing signals, e.g. pulsed, are fed to a monitoring electrode immersed in the solution mixture containing the immunoreactants. The labelled reactant in the mixture is labelled with a reversible electroactive tag, i.e., the label is chosen to give a fast and reversible electron transfer at the surface of the electrode under the influence of the perturbing alternating voltage. The monitored response to such an alternating voltage perturbation is an alternating current which waveshape is generally sinusoidal, but other waveshapes and/or types of signal modulation may be used.

The frequency of the perturbing signal is desired to be high, usually of the order of about 1 KHz or more. The higher frequency signal is desirable, because it greatly improves the sensitivity of the measurement of the immunoreaction. In order that these higher frequency signals may be utilized, however, will depend upon the ability of the electroactively-labelled immunoreactant to transfer electrons at the perturbation frequency at the monitoring electrode surface. An electroactive label is chosen which has a high heterogeneous rate constant of electron transfer, so that the labelled immunoreactant will be able to respond to the high frequency of the interrogation signal.

The frequency of the signal is related to the rate constant of electron transfer for each electroactive label, and, hence, the labelled immunoreactant, as taught by the reference to: A. J. Bard, Editor; Marcel Dekker, *Electroanalytical Chemistry*, Vol. I, Chapter 1, by D. E. Smith, Page 30.

When the mixture has been allowed to incubate, the changes in the free labelled Ag* will cause a change in the current signal. The change in this current signal is used to determine the unknown sample constituent.

This technique has assumed that the labelled-antigen Ag* is free in solution, i.e., current measurements are diffusion dependent. Large molecules of Ag* may not, however, migrate quickly through the solution (high diffusion coefficient) towards the monitoring electrode, and consequently, the sensitivity of the measurement may be poor for these larger molecules.

Enhancing Sensitivity of the Measurement

1. To further improve the sensitivity of the measurement, the labelled antigen may be covalently linked to, or immobilized upon, the monitoring electrode to eliminate the current signal dependency on the diffusion process. The binding of the labelled-antigen Ag* with the antibody Ab in solution inhibits the ability of the Ag* to transfer electrons at the electrode surface. This inhibition can be more easily monitored than the conventional method of measuring the free (not-immobilized) labelled antigen Ag* in solution. The binding of the labelled antigen Ag* may be accomplished via a cyanuric chloride as follows (D.C.S. Tse, T. Kuwana, *Anal. Chem.*, 50, 1315 (1978)):

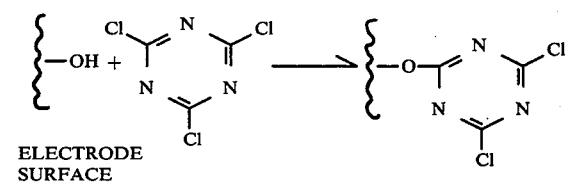

ELECTRODE SURFACE

The amine (NH₂) part of the antigen will then link to the electrode:

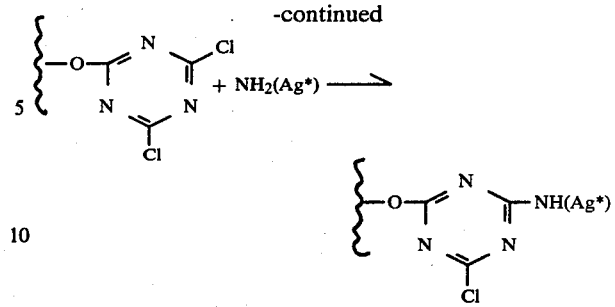

Many such chemical links, including, e.g. silanization and amidization, have appeared in the literature: J. R. Lenhard, R. W. Murray, *JEAC* 78, 195 (1977); P. R. Moses, R. W. Murray, *JEAC* 77, 393 (1977).

2. To further increase electron transfer, the antigen may be labelled with a plurality of electroactive groups by attaching a label to different chemical residues of the protein of the antigen molecule, such as $NH_2$, COOH, SH, etc.:

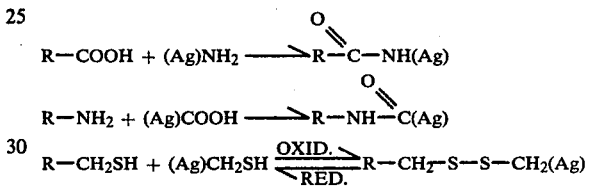

where: R is an electroactive label.

Similarly, an electroactive label "R" may be attached to the antigen via the following reaction:

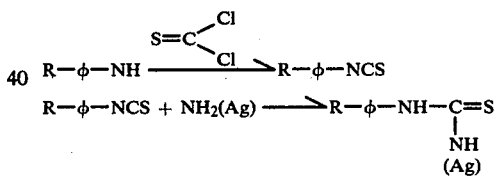

Two electroactive labels R may be attached to one $NH_2$ grouping of the protein (antigen) by the following reaction:

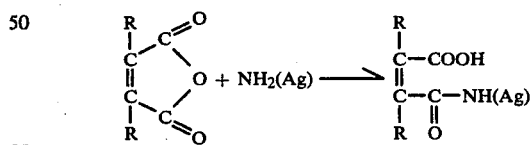

It is also known that a branched molecule similar to the above can contain a plurality of electroactive groups, which molecule can then be attached to the antigen via a single or multiple link as shown.

Reversible labels R may comprise electroactive transition metal chelates, where the metal may be chosen, for example, from a group consisting of: Fe, Co, Cu, Mo, Cd, V, Zn, Cr, Mn, and Ni, etc. The ligand of the chelate may be chosen from a group consisting of: porphyrins, pyridyls, and pyridines. Other chelates may be formed with ligands such as O-phenanthroline and 8-hydroxyquinoline which may also be used as labels R.

A typical label R can be a Cu (II) Bis-Terpyridyls complex, formed from the ligand 2,2',2''-Terpyridine. The complex is shown below:

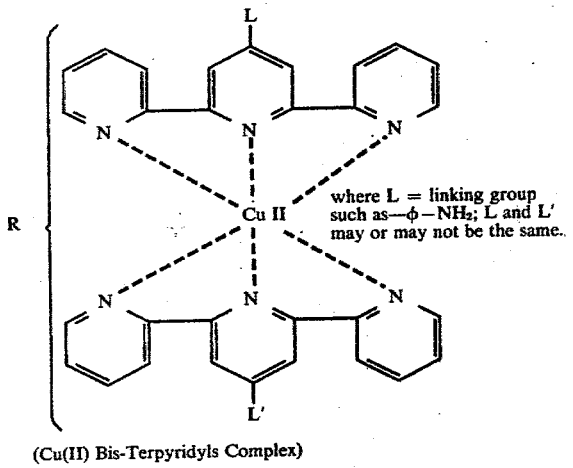

(Cu(II) Bis-Terpyridyls Complex)

Another typical label R can be:

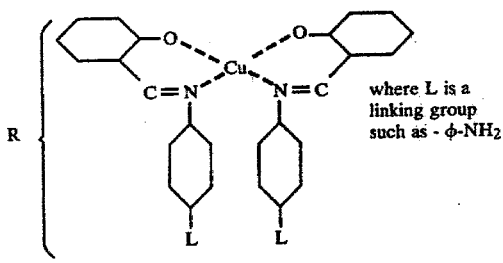

Organic electroactive labels, e.g. quinones, may also be used although the electron transfer may not be as facile as the complexes. On the other hand, organic tags are not susceptible to dissociation of the ligands and thus the loss of the label.

Other labelling techniques such as those shown for metallohaptens can also be used, according to the article in *Nature;* "Metalloimmunoassays", Vol. 270 (8 Dec. 1977).

3. An ancillary reaction may be arranged to further enhance the measurement of the immunoreaction. An excess of oxidant is added to the solution containing the immunoreactants. After the immunoreaction has occurred, the oxidant will reoxidize the free labelled antigen Ag* as the free Ag* loses electrons at the monitoring electrode surface. Therefore, a catalytic electrode process will be created due to the redox capability of the labelled antigen Ag* to accept or donate electrons. The rapid regeneration (oxidation) of the electrochemically reduced Ag* will increase the effective concentration of the labelled antigen at the monitored electrode surface, whereby an enhanced signal is realized. The reaction is given by the following equation:

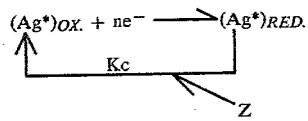

wherein:
$(Ag^*)_{OX}$ is the oxidized labelled antigen Ag*;
$(Ag^*)_{RED}$ is the reduced labelled antigen Ag*;
$ne^-$ is the number of electrons the labelled antigen $(Ag^*)_{OX}$ will accept at the monitoring electrode surface; and
z is an electroinactive oxidant present in solution for converting $(Ag^*)_{RED}$ to $(Ag^*)_{OX}$ such as a peroxide.

Where the rate constant of reoxidation $k_c$ is of the order of $10^{-4}$ sec$^{-1}$, the electrode sensitivity will be theoretically enhanced to less than $10^{-9}$ M/L (assuming relaxation techniques are used to monitor the reaction, see A. J. Bard, Editor; Marcel Dekker, *Electroanalytical Chemistry*, Vol. I, Chapter 1, by D. E. Smith, Pages 1–155). The electroactively-labelled immunoreactant may be either free in the solution or attached to the monitoring electrode.

Alternately, a reductant may be added to the solution for regenerating an oxidized labelled antigen.

Having thus described the invention, what is desired to be protected by Letters Patent is presented by the appended claims.

1. A voltammetric monitoring electrode for measuring electrochemical changes resulting from an immunoreaction between complementing immunoreactants, said voltammetric monitoring electrode comprising an electroactively-labelled immunoreactant attached to a surface thereof.

2. The voltammetric monitoring electrode of claim 1, wherein said electroactively-labelled immunoreactant comprises at least one transition metal chelate linked to said immunoreactant.

3. The voltammetric monitoring electrode of claim 2, wherein said transition metal chelate consists of a metal chosen from a group of metals consisting of: Fe, Co, Cu, V, Zn, Cr, Mo, Cd, Mn, and Ni.

4. The voltammetric monitoring electrode of claim 2, wherein said transition metal chelate consists of a ligand chosen from a group of ligands consisting of: pyridyls, porphyrins, and pyridines.

5. An electroactively-labelled immunoreactant having more than one electroactive group attached thereto for the purpose of increasing the ability of the immunoreactant to transfer electrons at a surface of a monitoring electrode during a voltammetric immunossay, and hence, increase the sensitivity of measurement of said immunoreactant.

6. The electroactively-labelled immunoreactant of claim 5 comprising at least one transition metal chelate linked to said immunoreactant.

7. The electroactively-labelled immunoreactant of claim 6, wherein said transition metal chelate consists of a metal chosen from a group of metals consisting of: Fe, Co, Cu, V, Zn, Cr, Mo, Cd, Mn, and Ni.

8. The electroactively-labelled immunoreactant of claim 6, wherein said transition metal chelate consists of a ligand chosen from a group of ligands consisting of: pyridyls, porphyrins, and pyridines.

* * * * *